Jan. 19, 1960 H. C. SWIM Plant Pat. 1,896
ROSE PLANT
Filed April 20, 1959
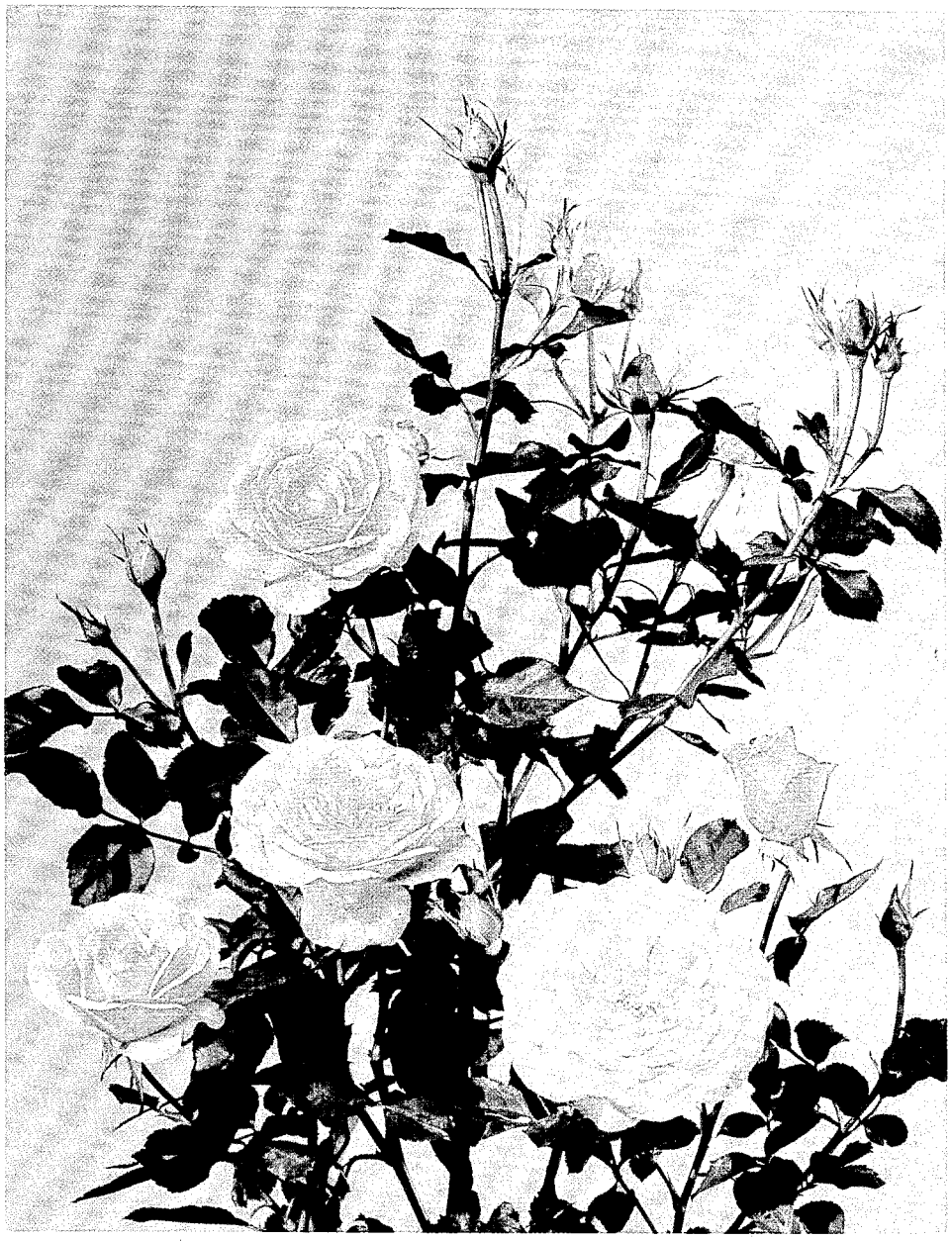
Inventor.
H. C. Swim
By: Robb & Robb
Attorneys.

United States Patent Office

Plant Pat. 1,896
Patented Jan. 19, 1960

1,896

ROSE PLANT

Herbert C. Swim, Ontario, Calif., assignor to Armstrong Nurseries, Inc., Ontario, Calif., a corporation of California Application April 20, 1959, Serial No. 807,740

1 Claim. (Cl. 47—61)

The present invention relates to a new and distinct variety of rose plant of the floribunda class, which was originated by me by the deliberate planting and growing of seed derived from open-pollinated flowers of an unnamed seedling which is the subject of my copending plant patent application Serial No. 785,770, filed January 8, 1959.

The general objective of my efforts in this connection was to produce an improved pink floribunda rose which maintains the attractive bud and half-open flower form of the parent variety, recombined with the greater floriferousness and double petalage of the grandparent variety, "Pinocchio" (Plant Patent No. 484), while at the same time having the flowers attractively and evenly spaced over a healthy, vigorous, bushy, compact plant. This objective was substantially achieved along with other desirable improvements, as evidenced by the following unique combination of characteristics which are outstanding in the new variety and which distinguish it from its parent, as well as from all other varities of which I am aware:

(1) A vigorous, compact, bushy, much-branched habit of plant growth, with the plant having a medium size;

(2) Attractive, dark green, disease-resistant foliage of medium size;

(3) Flowers borne abundantly on stems of from short to medium length in small clusters which are evenly spaced over the plant in an attractive manner;

(4) Very double flowers of medium size, and having an attractive urn-shaped bud form which opens into a well-formed symmetrical open flower; and (5) A flower color which is an attractive and distinctive shade of light red or dark pink which tends to fade evenly to a lighter color as the flower ages.

In comparison with its parent variety, the plant of the new variety is of medium size whereas that of the parent is very large; the flowers are borne somewhat more abundantly and in somewhat larger clusters; the flowers are very double, instead of semi-double or double as in the parent variety; and the flower color is a dark pink or light red, whereas that of the parent is a lighter pink color.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety, in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbrieviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Polyantha.

Breeding: An open-pollinated seedling of an unnamed seedling which is the subject of pending plant patent application Serial No. 785,770, filed January 8, 1959.

Propagation: Holds its distinguishing characteristics through succeeding propagations by budding.

*Flower*

Locality where grown and observed: Ontario, California.

Flowers borne: Usually from 3 to 5 or more to stem; in irregular and somewhat flat clusters; on stems ranging from short to medium length and of normal strength.

Quantity of bloom: Abundant, outdoors.

Continuity: Nearly continuous during growing season.

Fragrance: Moderate.

Bud:

*Peduncle.*—From short to average length; from slender to average caliper; erect; usually smooth; with from few to several stipitate glands and sometimes few fine hairs. Color—near Sayal Brown, Plate XXIX (Ridgway) overlaid with near Madder Brown, Plate XIII (Ridgway) on said exposed to sun.

*Before calyx breaks.*—Size—small. Form— short; ovoid.

*As calyx breaks.*—Color—between Scarlet, Plate 19/1, page 19 (Wilson) and Geranium Lake, Plate 20/1, page 20 (Wilson), with areas first exposed sometime near Oxblood Red, Plate 00823/1, page 191 (Wilson).

*Sepals.*—Inner surface—with fine, woolly tomentum. Outer surface—usually with several stipitate glands. Alternate margins—lined with stipitate glands and slender foliaceous appendages. Other margins—lined with fine, woolly tomentum.

*As first petal opens.*—Size—from small to average. Form—from ovoid to urn-shaped. Color: outside — between Crimson, Plate 22/2, page 22 (Wilson) and Rose Madder, Plate 23/1, page 23 (Wilson), with small area at base near Canary Yellow, Plate 2/3, page 2 (Wilson); inside—between Carmine, Plate 21/2, page 21 (Wilson) and Crimson, Plate 22/2, page 22 (Wilson), with small area at base near Canary Yellow, Plate 2/2, page 2 (Wilson).

*Opening.*—Opens up well; is not prevented from opening by cold, hot, wet or dry weather.

Bloom:

*Size (when fully open).*—Average; from 2½ inches to 3½ inches.

*Petalage.*—Very double; from 40 to 54 petals plus from 2 to 6 petaloids; arranged regularly.

*Form.*—High-centered at first, but becoming from flat to cupped; petals being at first somewhat loosely cupped, with tips rolled outward, but becoming later at maturity more loosely flat, with tips slightly rolled outwardly.

Petals:

*Texture.*—Medium thickness. Inside—slightly satiny. Outside—satiny.

*Shape.*—Outer—broadly obovate, with apex flat. Intermediate—obovate, with apex rounded and sometimes with 1 or 2 notches. Inner—narrowly obovate and irregular, with apex rounded, and sometimes with 1 or 2 notches.

This description of a newly opened flower was made from a rose grown outdoors in the month of October at Ontario, California:

*Color.*—Outer petal: outside surface—between Crimson, Plate 22/2, page 22 (Wilson) and Rose Madder, Plate 23/2, page 23 (Wilson), with occasional markings of near Crimson, Plate 22, page 22 (Wilson) where first exposed while in the bud stage, and with small area at base near Canary Yellow, Plate 2/3, page 2 (Wilson); inside surface—between Carmine, Plate 21/3, page 21 (Wilson) and Rose Madder, Plate 23/3, page 23 (Wilson), with small area at base near Canary Yellow, Plate 2/3, page 2 (Wilson). Intermediate petal: outside surface—between Crimson, Plate 22/2, page 22 (Wilson) and Rose Madder, Plate 23/2, page 23 (Wilson), with small area at base near Canary Yellow, Plate 2/3, page 2 (Wilson); inside surface—between Carmine, Plate 21/2, page 21 (Wilson) and Crimson, Plate 22/2, page 22 (Wilson), with small area at base near Canary Yellow, Plate 2/2, page 2 (Wilson). Inner petal: outside surface—between Crimson, Plate 22/1, page 22 (Wilson) and Rose Madder, Plate 23/1, page 23 (Wilson), with small area at base near Canary Yellow, Plate 2/3, page 2 (Wilson); inside surface—between Carmine, Plate 21/1, page 21 (Wilson) and Crimson, Plate 22/1, page 22 (Wilson), with small area at base near Canary Yellow, Plate 2/2, page 2 (Wilson).

This description was made from a rose that was open for 3 days outdoors in the month of October at Ontario, California:

*Color.*—Outer petal: outside surface—between Rose Madder, Plate 23/2, page 23 (Wilson) and Rose Madder, Plate 23/3, page 23 (Wilson), with occasional markings of near Crimson, Plate 22, page 22 (Wilson) where first exposed while in the bud stage; inside surface—between Crimson, Plate 22/3, page 22 (Wilson) and Rose Madder, Plate 23/3, page 23 (Wilson), with small area at base near Canary Yellow, Plate 2/3, page 2 (Wilson). Inner petal: outside surface—between Carmine, Plate 21/2, page 21 (Wilson), and Rose Madder, Plate 23/3, page 23 (Wilson), with small area at base near Canary Yellow, Plate 2/3, page 2 (Wilson); inside surface—between Carmine, Plate 21/2, page 21 (Wilson) and Crimson, Plate 22/2, page 22 (Wilson), with small area at base near Canary Yellow, Plate 2/3, page 2 (Wilson).

*General color effect.*—Newly opened flower—between Carmine, Plate 21/1, page 21 (Wilson) and Rose Madder, Plate 23/3, page 23 (Wilson). 3-days open—between Carmine, Plate 21/2, page 21 (Wilson) and Rose Madder, Plate 23/3, page 23 (Wilson).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—from 5 to 7 days in November.

*Reproductive organs*

Stamens: From few to average number; arranged regularly about pistils.

Filaments: From short to medium length; from 4 to 10 mm. in length; most with anthers. Color—near Sulphur Yellow, Plate 1/2, page 1 (Wilson).

Anthers: From small to medium size; all open approximately at once. Color: upper side—margins near Saffron Yellow, Plate 7/2, page 7 (Wilson), with remainder near Aureoline, Plate 3/2, pages 3 (Wilson); underside—margins near Saffron Yellow, Plate 7/2, page 7 (Wilson), with remainder near Aureolin, Plate 3/2, page 3 (Wilson).

Polen: From sparse to moderate quantity. Color—near Saffron Yellow, Plate 7/1, page 7 (Wilson).

Pistils: From average number to many; approximately 60 in number.

Styles: Moderately even; from short to average length; from 8 to 12 mm. in length; from thin to average caliper; bunched. Color—upper ⅓ of style near Scarlet, Plate 19/2, page 19 (Wilson), with remainder near Canary Yellow, Plate 2/3, page 2 (Wilson).

Stigma: Color—near Maize Yellow, Plate 607/2, page 69 (Wilson).

Ovaries: Usually all enclosed in calyx.

Hips: Short; globular; smooth; walls thick and fleshy. Color (½ Mature)—near Kildare Green, Plate XXXI (Ridgway), overlaid with near Kaiser Brown, Plate XIV (Ridgway) on side exposed to sun.

Sepals: Falling soon; from medium length to long; usually curled. Color: inside—near light Grape Green, Plate XLI (Ridgway); outside—near Absinthe Green, Plate XXXI (Ridgway), with areas of near Vinaceous Brown, Plate XXXIX (Ridgway).

Seeds: Few; from 2 to 6 per hip; medium size.

*Plant*

Foliage:

*Leaves.*—Compound of usually 3 to 7 leaflets; normal abundance; medium size; somewhat leathery; semi-glossy.

*Leaflets.*—Shape—from oval to obovate, with apex usually obtuse. Base—from round to obtuse. Margin—simply serrate.

*Color.*—Mature: upper surface—near Elm Green, Plate XVII (Ridgway); under surface—near light Hellebore Green, Plate XVII (Ridgway). Young: upper surface—near light Yellowish Olive, Plate XXX (Rigway), overlaid with near Prussian Red, Plate XXVII (Ridgway); under surface—near Prussian Red Plate XXVII (Ridgway).

*Rachis (the supporting stem of the compound leaf).*—Average size. Upper side—grooved; with several stipitate glands on edges. Under side—moderately smooth; with stipitate glands, and from 2 to 5 small prickles.

*Stipules.*—Short; medium-width; with short points turning out at an angle of less than 45°.

*Disease resistance.*—Better-than-average resistance to mildew, as compared with other varieties grown under comparable cultural conditions at Ontario, California.

Growth:

*Habit.*—Bushy; upright-spreading; much-branched.

*Growth.*—Moderately vigorous.

*Canes.*—Medium caliper.

*Main stems.*—Color—near Rainette Green, Plate XXXI (Ridgway). Large prickles—several; from short to medium length; hooked slightly downward; with narrow base of medium length; color—near Fawn, Plate XL (Ridgway). Small prickles—several; color—near Fawn, Plate XL (Ridgway). Hairs—none, but surfaces of stems are covered with many stipitate glands.

*Branches.*—Color—near Biscay Green, Plate XVII (Ridgway). Large prickles—several; medium-length; hooked slightly downward; with narrow base of medium length; color—near Dark Vinaceous, Plate XXVII (Ridgway). Small prickles—from few to several; color—near Dark Vinaceous, Plate XXVII (Ridgway). Hairs—none, but surface covered with many stipitate glands.

*New shoots.*—Color—near Citrine Drab, Plate XL (Ridgway), overlaid with near Madder Brown, Plate XIII (Ridgway) on side exposed to sun. Large prickles—few; short; hooked slightly downward; with short, narrow base; color—near Mineral Red, Plate XXVII (Ridgway). Small prickles—from none to few; color—near Mineral Red, Plate XXVII (Ridgway). Hairs—none, but surface of shoots usually covered with from several to many stipitate glands.

I claim:

A new and distinct variety of rose plant of the floribunda class, substantially as herein shown and described, characterized particularly as to novelty by its unique combination of vigorous, compact, bushy, medium sized and much-branched plant habit, attractive, medium sized, dark green, disease-resistant foliage, a habit of bearing flowers abundantly on stems ranging from short to medium length and in small clusters evenly spaced over the plant, said flowers being of medium size and very double, and being urn-shaped in the bud stage, but opening into a well-formed symmetrical open flower, and a distinctive light red or dark pink general color tonality of the flowers, with a tendency to fade evenly to a lighter color as the flowers age.

No references cited.